(12) United States Patent
Kruppa et al.

(10) Patent No.: US 7,368,290 B2
(45) Date of Patent: May 6, 2008

(54) STRUCTURAL DETERMINATION OF INTACT PROTEINS USING MASS SPECTROMETRY

(75) Inventors: Gary Kruppa, San Francisco, CA (US); Joseph S. Schoeniger, Oakland, CA (US); Malin M. Young, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 660 days.

(21) Appl. No.: 10/437,268

(22) Filed: May 12, 2003

(65) Prior Publication Data

US 2004/0229369 A1 Nov. 18, 2004

(51) Int. Cl.
  G01N 33/00 (2006.01)
  G01N 24/00 (2006.01)
(52) U.S. Cl. .......................................... 436/86; 436/86
(58) Field of Classification Search ................... 436/86
  See application file for complete search history.

(56) References Cited

U.S. PATENT DOCUMENTS

| | | | |
|---|---|---|---|
| 5,504,327 A | 4/1996 | Sproch et al. | |
| 5,821,063 A | 10/1998 | Patterson et al. | |
| 6,271,037 B1 | 8/2001 | Chait et al. | |
| 6,291,189 B1 | 9/2001 | Woods, Jr. | |
| 6,312,893 B1 | 11/2001 | Van Ness et al. | |
| 6,322,970 B1 | 11/2001 | Little et al. | |
| 6,329,146 B1 | 12/2001 | Crooke et al. | |
| 6,331,400 B1 | 12/2001 | Woods, Jr. | |
| 6,379,971 B1 | 4/2002 | Schneider et al. | |
| 6,391,649 B1 | 5/2002 | Chait et al. | |
| 6,713,256 B1 * | 3/2004 | Hoffmann et al. | ............. 435/6 |

OTHER PUBLICATIONS

Reid et al. "Top down protein characterization via tandem mass spectrometry," Journal of Mass Spectrometry, 37:663-675 (2002).*
Lacroix et al. "Structure and Assembly of the Catalytic Region of Human Complement Protease Clr: A Three Dimensional Model Based on Chemical Cross-linking and Homology Modeling," Biochemistry, 36: 6270-6282, (1997).*
Nguyen et al. "Protein mass spectrometry: applications to analytical biotechnology," Journal of Chromatography, 705: 21-45 (1995).*
Kruppa et al. "A top down approach to protein structural studies using chemical cross-linking and Fourier Transform mass spectrometry," Rapid Communications in Mass Spectrometry, 17: 155-162, (2002).*
Kelleher, et al., "Top Down versus Bottom Up Protein Characterization by Tandem High-Resolution Mass Spectrometry". Journal of the American Chemical Society, 1999, 121 806-812.
Young, et al., "High Throughput Protein Fold Identification by Using Experimental Constraints Derived from Intramolecular Cross-links and Mass Spectrometry," Proc. Natl Acad Sci (USA) 2000 97 5802-5806.
Keefe, Tim, "Nanospray Analysis of Proteins Using Water and Buffered Solutions", Application Note BT-04, Bruker Daltonics, Inc., Billerica, Mass., 1999.
Ingendoh, et al., "Identification of Proteins by Fast LC/MS/MS Screening of their Enzymatic Digests and Database Search", Application Note #LCMS-01, Bruker Daltonik GmbH 1999.
Schneider, et al., "On-line, Near orthogonal Nano-electrospray couple with Ion Trap MS for Proteomic Analysis", Application Note #LCMS-12, Bruker Daltonik GmbH, 1999.
"High Mass Accuracy Approach to Proteomics Using Fourier Transform Mass Spectrometry", Application Note FTMS-27, Bruker Daltonics, Inc., 1999.
Keefe, Tim, "Investigating Changes in Protein Conformation", Application Note BT-03, Bruker Daltonics, Inc., Billerica, Mass., 1999.
Ewing, et al., "Peptide Fingerprinting on the OmniFLEX(TM): Bench-top Protein Identification", Applications Note MT-1072, Bruker Daltonics, Inc., 1999.
Faulon, J.L., et al., "Constrained Walks and Self-Avoiding Walks: Implications for Protein Structure Determination." Journal of Physics, V. 34, 2002, pp. 1-19.
Young, M.M., et al., "High-throughput Protein Fold Identification Using Experimental Constraints Derived From Intramolecular Cross-linking and Mass Spectrometry." Proceedings of the National Academy of Science, V. 97(11), 2000, pp. 802-806.

* cited by examiner

*Primary Examiner*—Jill Warden
*Assistant Examiner*—Keri A Moss
(74) *Attorney, Agent, or Firm*—Ward & Olivo; David M. Hill

(57) ABSTRACT

The present invention relates to novel methods of determining the sequence and structure of proteins. Specifically, the present invention allows for the analysis of intact proteins within a mass spectrometer. Therefore, preparatory separations need not be performed prior to introducing a protein sample into the mass spectrometer. Also disclosed herein are new instrumental developments for enhancing the signal from the desired modified proteins, methods for producing controlled protein fragments in the mass spectrometer, eliminating complex microseparations, and protein preparatory chemical steps necessary for cross-linking based protein structure determination.

Additionally, the preferred method of the present invention involves the determination of protein structures utilizing a top-down analysis of protein structures to search for covalent modifications. In the preferred method, intact proteins are ionized and fragmented within the mass spectrometer.

19 Claims, 13 Drawing Sheets

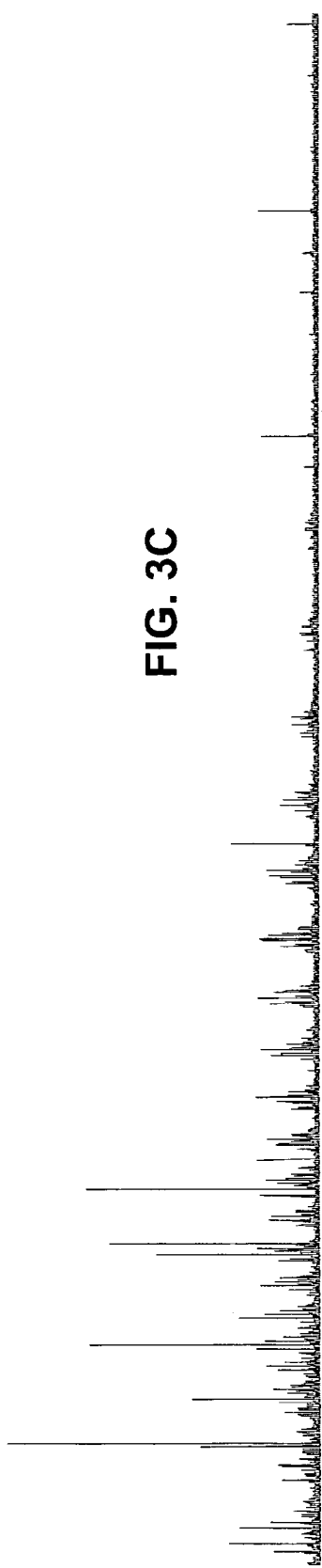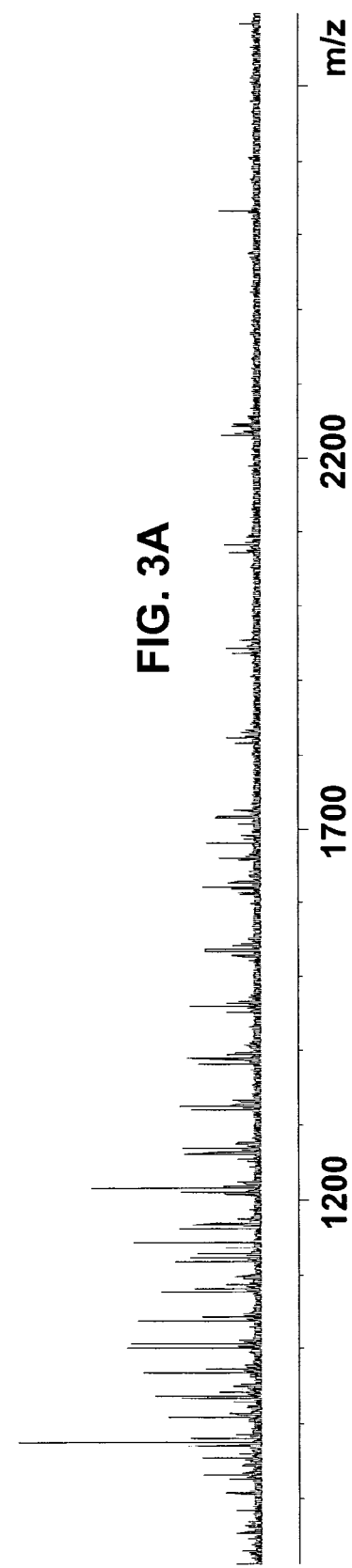
FIG. 3A
FIG. 3B
FIG. 3C

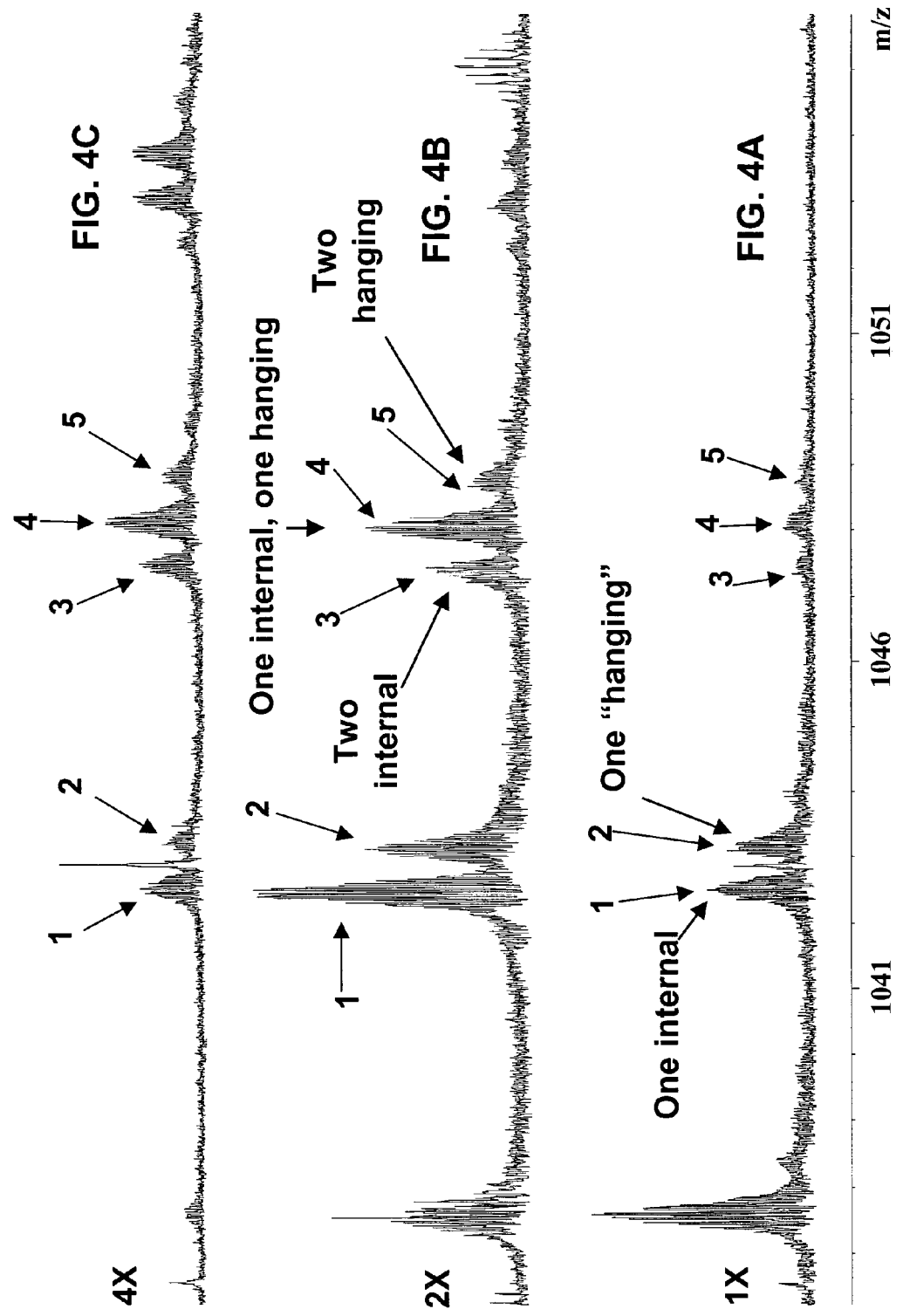

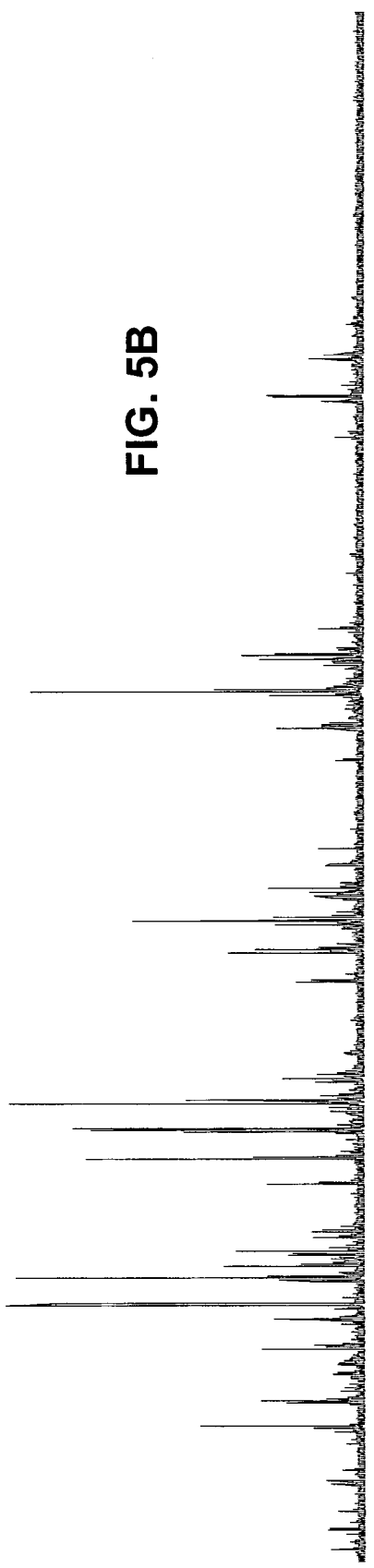

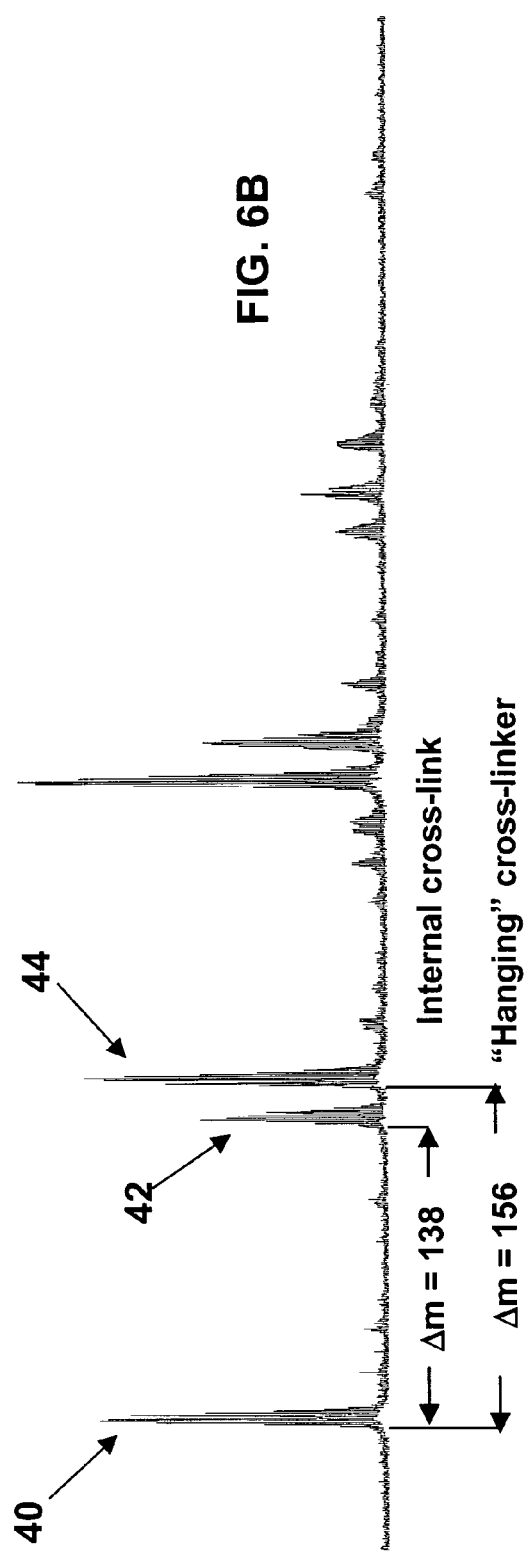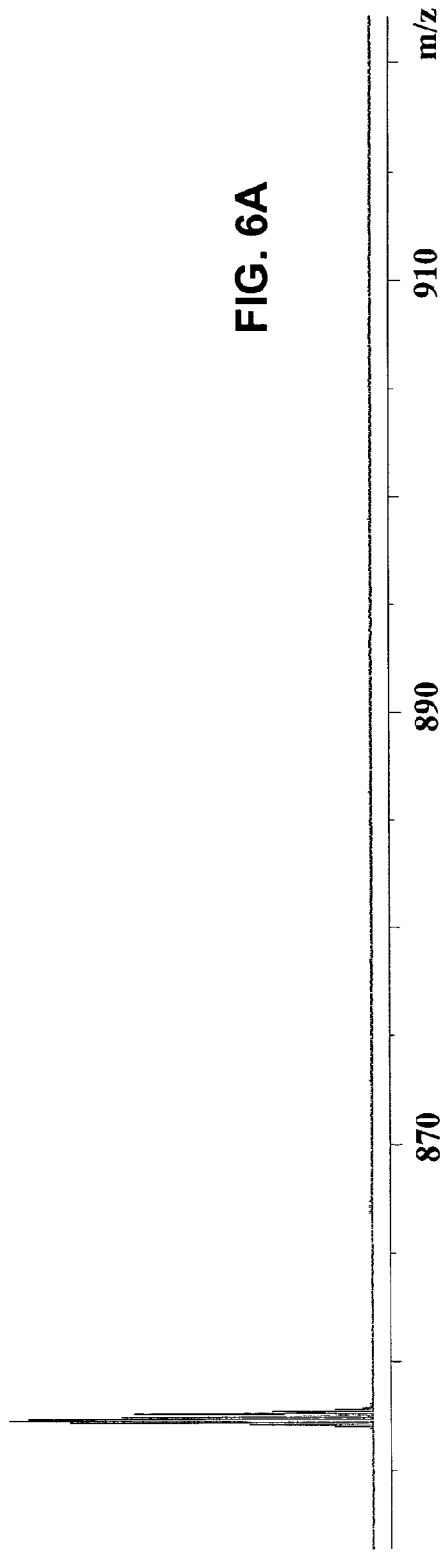

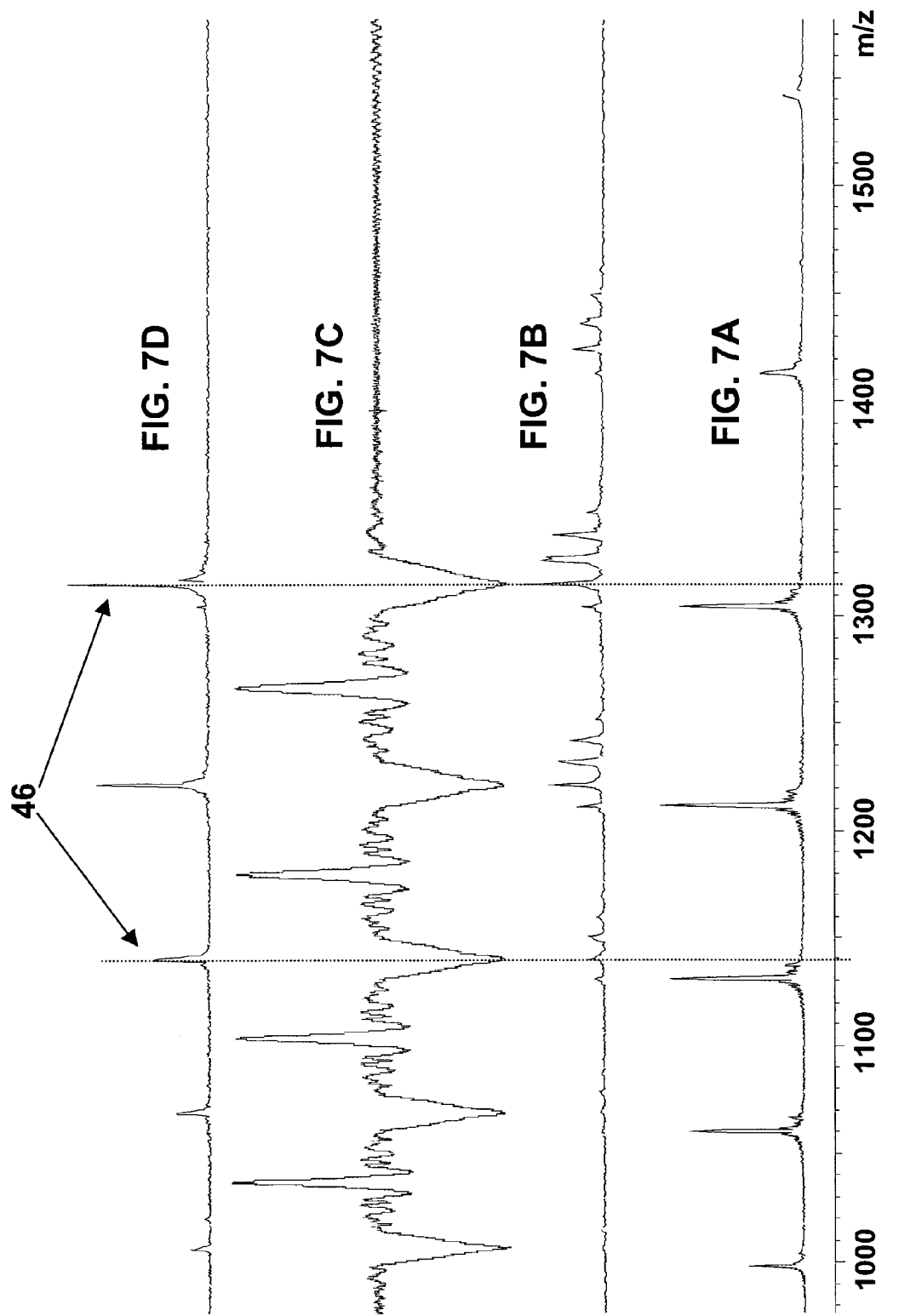

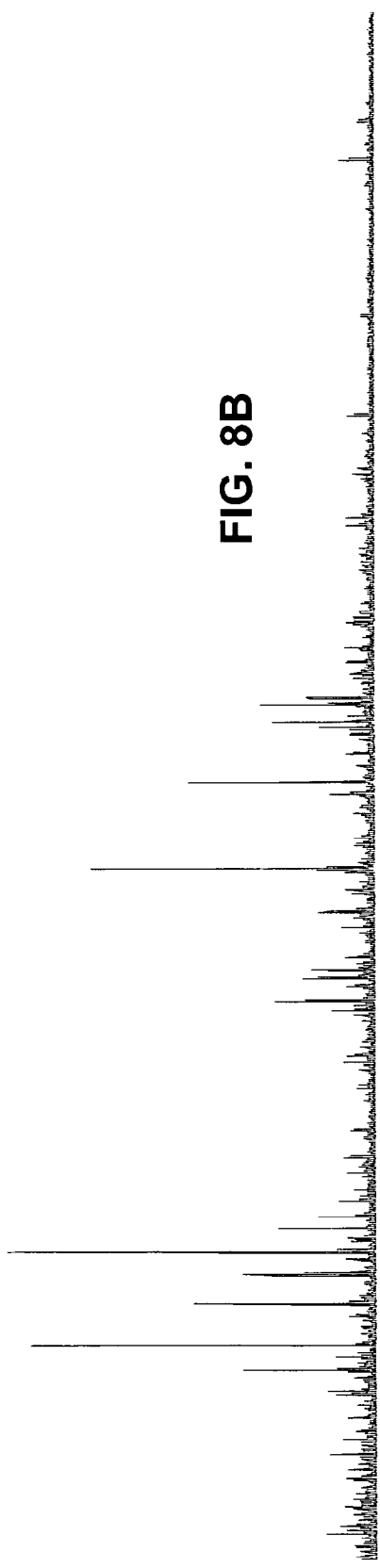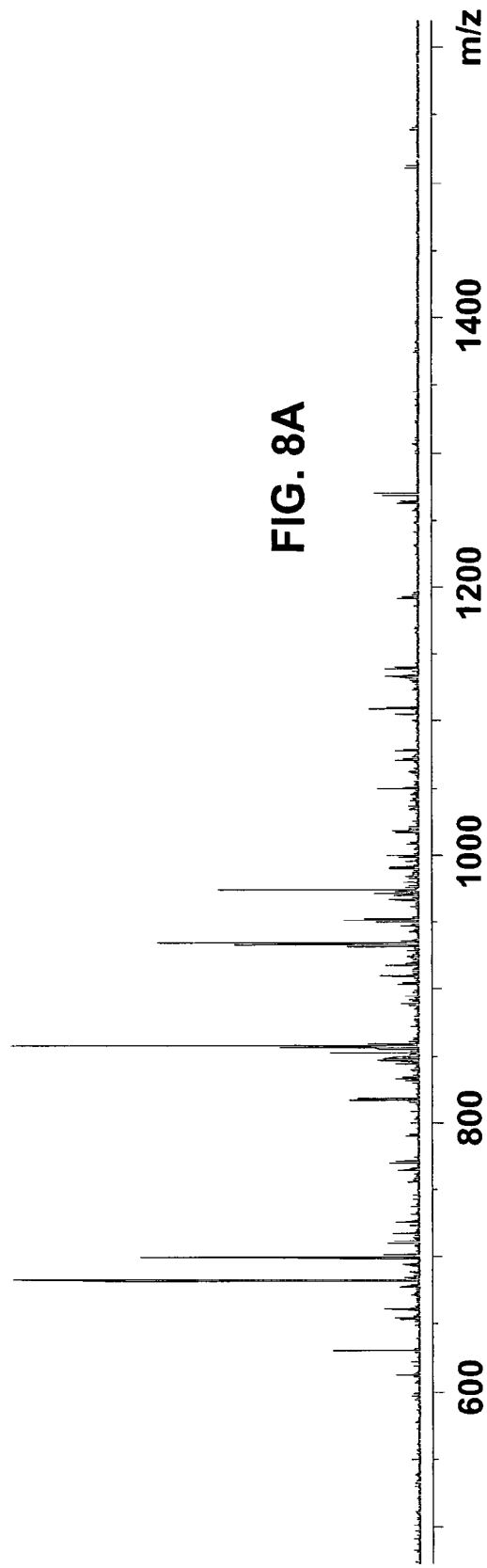

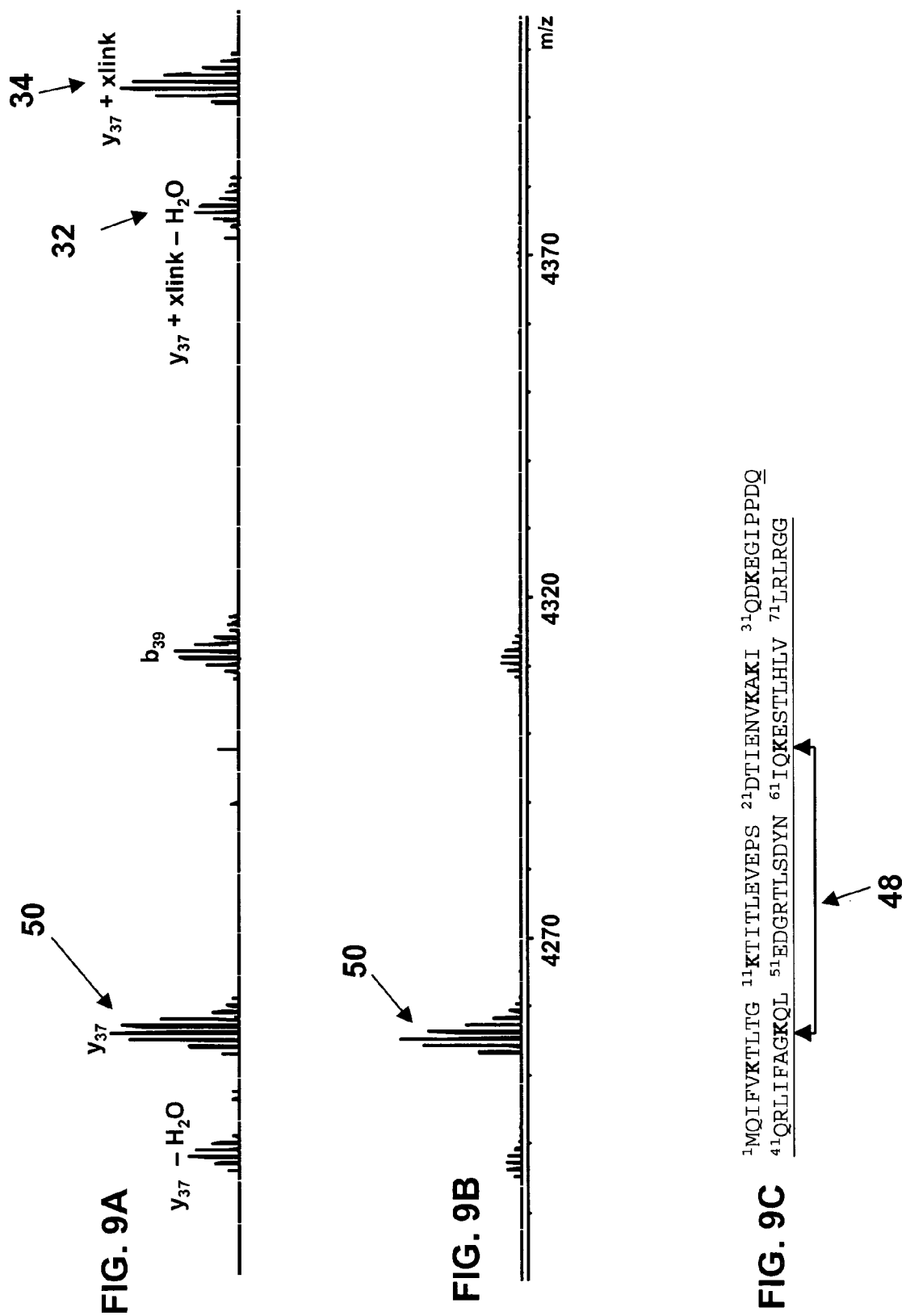

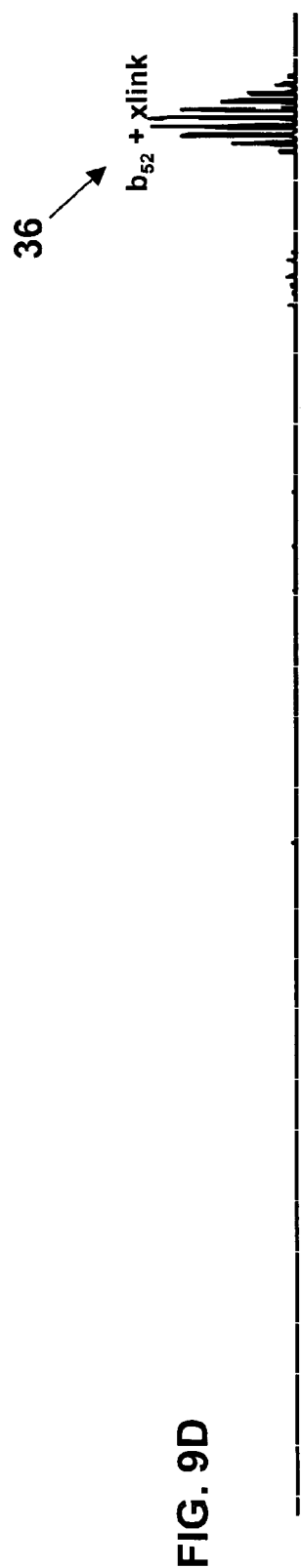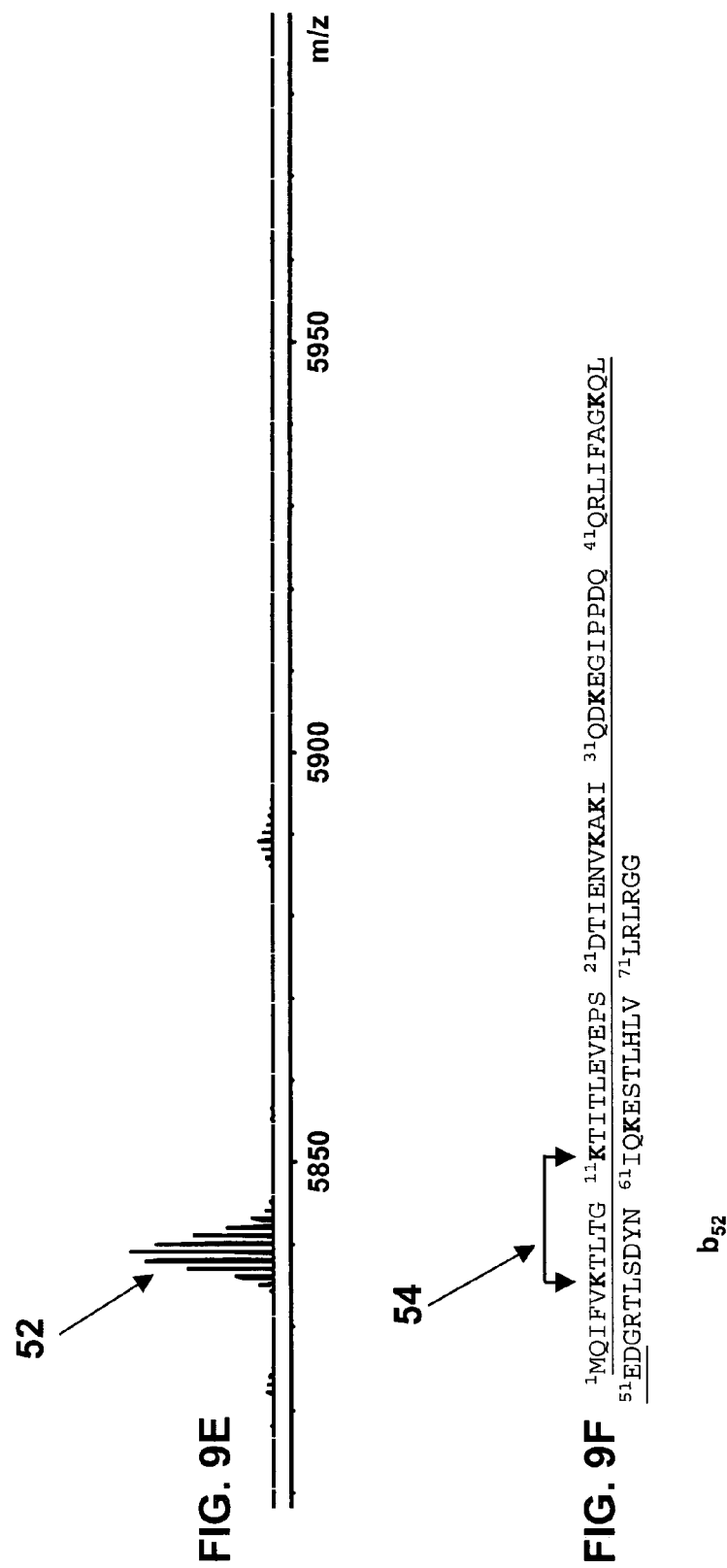
FIG. 9D
FIG. 9E
FIG. 9F

STRUCTURAL DETERMINATION OF INTACT PROTEINS USING MASS SPECTROMETRY

GOVERNMENT RIGHTS

This invention was made with government support under Contract No. DE-AC04-4AL85000 by the United States Department of Energy. The government has certain rights in the invention.

BACKGROUND OF THE INVENTION

The present invention relates to the field of protein structure determination via mass spectrometry. More particularly, the present invention provides the ability to analyze the structure of intact proteins, using distance constraints obtained from the analysis of MS/MS spectra of proteins after cross-linking, via a top-down approach.

Proteins are a class of compounds composed of α-amino acid residues, covalently bonded through amide linkages after elimination of water between the carboxy group of one amino acid and the amino group of another amino acid. A protein can be considered a polymer consisting of a larger number of α-amino acid residues.

Proteins are complex polymers, containing carbon, hydrogen, nitrogen, oxygen, and sulfur, and comprised of linear chains of amino acids connected by peptide links.

Understanding the structure of proteins is important for a complete understanding of the physiological reactions involving proteins. The structure of a protein is typically described by its primary, secondary, tertiary, and quaternary structures. The amino acid sequence of the protein defines the primary structure. Proteins seldom form random coils and the high specificity of their function depends on a defined conformation of the polypeptide chain, in a secondary structure. The most common types of secondary structures are α-helices and β-sheets. The elements of secondary structure may be connected via loops and turns of various types into a larger tertiary structure. The present invention is concerned with elucidating the secondary and tertiary structure of a given protein. Proteins may also consist of several folded polypeptide chains (known as sub-units) which associate with each other not through covalent peptidic bonds, but through non-covalent interactions. The present invention can also be used to probe the quaternary structure.

Determination of the three-dimensional structures of proteins has traditionally been accomplished through the use of x-ray crystallography and nuclear magnetic resonance (NMR) spectroscopy, and both techniques produce high resolution data. However, the preparation of large amounts of pure analyte in a certain solution, or growth of a suitable crystal for analysis is difficult and time-consuming. After meeting these conditions, a substantial amount of data acquisition and analysis is required and it can take weeks to months to complete a picture of the molecular structure of a protein.

The number of novel proteins discovered in recent years has dramatically increased, and the time-consuming traditional techniques of structural determination discussed above are not keeping pace. An alternative approach to structure determination that could match the rate of the identification of new proteins is provided by the present invention. The present invention uses cross-linking reagents, which can provide sufficient low-resolution interatomic distance constraints to solve the tertiary structure of a protein when combined with state-of-the-art computational methods.

This invention relates to a specific approach to the new method for protein structure determination involving a top-down approach, versus a bottom-up approach. The entire crude cross-linked protein mixture is injected into an electrospray ionization Fourier transform mass spectrometer (ESI-FTMS) instrument, for example, and the cross-link positions localized by multiple stages of fragmentation and mass spectrometry.

A bottom-up approach has typically been used in applications such as protein identification via peptide mass mapping and protein structure elucidation using hydrogen/deuterium exchange, chemical labeling and cross-linking. In the bottom-up approach, after purification of a protein, the protein is digested by a proteolytic enzyme such as trypsin, and then masses of the resulting peptides are measured using mass spectrometry. Identifiable peptides from a single proteolysis typically represent only 50-90% of the protein sequence, complicating the identification of mass modifications in the remainder of the protein sequence. In addition, false mass values commonly appear in spectra, which result from self-proteolysis and protein impurities.

In a recent paper, Kelleher et al. (*J. Am. Chem Soc.* 1999, 121, 806-812) describe the advantages of the top-down versus bottom-up approach to protein characterization by tandem high-resolution mass spectrometry. In the top-down approach Kelleher et al. chose conditions that gave limited dissociation of the ionized protein, which gave a small number of large fragments where one or more complementary sets of fragments, the masses of which sum to the value of the expected mass of the protein, can easily be identified.

In the present invention, chemical cross-linking is performed before sample cleanup. Purification of the cross-linked species occurs in the gas phase within the mass spectrometer. The proteins are also 'digested' within the mass spectrometer, using, but not limited to, techniques such as collision induced dissociation (CID), infrared multiphoton dissociation (IRMPD), and electron capture dissociation (ECD). The fragmentation conditions can be varied to give minor fragmentation, yielding large complementary fragments, or extensive fragmentation useful for localization of the cross-links.

More recently, the utilization of chemical cross-linking in conjunction with mass spectrometry to elucidate three-dimensional protein structures has been disclosed Patterson et al., U.S. Pat. No. 5,821,063, disclose methods for sequencing polymers utilizing mass spectrometry. In particular, the methods of Patterson et al. involve varying ratios of hydrolyzing agent to polymer and integrating mass spectral data obtained from the analysis of a series of hydrolyzed polymer fragments. The methods of Patterson et al. provide an optional use of statistical interpretation paradigms and computer software. Patterson et al. also require the hydrolysis of polymers before they are introduced into the mass spectrometer. The present invention, however, utilizing the top-down approach, does not require this step because intact proteins are injected into the mass spectrometer. Moreover, the present invention is capable of determining the three-dimensional structure of biological macromolecules. Therefore, the methods of the present invention, unlike Patterson et al., do not require preliminary hydrolysis and yield three-dimensional structural information.

Woods, Jr., U.S. Pat. Nos. 6,291,189 B1 and 6,331,400 B1, discloses methods of labeling polypeptides and proteins with heavy hydrogen to aid in the analysis of protein structure and the fine structure of protein binding sites. However, the methods disclosed require degradation of the polypeptide, or protein, into peptide fragments which are then analyzed by mass spectrometry in a bottom-up approach. Again, the methods of the present invention utilize the top-down approach, where analysis of intact proteins is possible.

Schneider et al., U.S. Pat. No. 6,379,971, disclose methods for sequencing proteins involving labeling proteins and subsequently analyzing the proteins in a mass spectrometer wherein the proteins undergo mass spectral fragmentation. Although Schneider et al. use in-source fragmentation, they use this technique in order to determine the primary structure of a polypeptide. In contrast to the present invention, the use of cross-linking and the top-down approach in mass spectroscopy teaches to the secondary and tertiary structure.

The advantage of the methods of the present invention over previously used methods is the utilization of high resolution mass spectrometry of intact proteins. New instrumental developments for enhancing the signal from the desired modified proteins, and methods for producing controlled protein fragments in the mass spectrometer, in order to eliminate complex microseparations, are disclosed herein. Also disclosed herein are preparatory chemical steps necessary for the analysis of the methods disclosed herein.

The use of chemical cross-links to elucidate protein structure has been previously disclosed in the art, and therefore, will not be discussed in great detail. Young et al. ("High Throughput Protein Fold Identification by Using Experimental Constraints Derived From Intramolecular Cross-Links and Mass Spectrometry," *Proc. Natl. Acad. Sci.* (USA), 2000, 97, 5802-5806) describe the use of chemical cross-links in the determination of protein structure. The approach, unlike the present invention, utilizes mass spectrometry of fragment ions of proteins, generated using chemical or enzymatic cleavage of proteins. According to the present invention, where the more efficient top-down approach is used, enzymatic digestion is unnecessary as intact proteins may be introduced into the mass spectrometer. Moreover, the complexities of preparatory separations may also be avoided, such as determining the proper conditions for enzymatic digestion with trypsin and the separation and purification of peptides with high-pressure liquid chromatography (HPLC).

SUMMARY OF THE INVENTION

The present invention relates to novel methods of obtaining distance constraints between amino acid residues of a protein to be used in determining the structure the protein. Specifically, the present invention allows for the analysis of intact proteins within a mass spectrometer. Therefore, preparatory separations are not necessary prior to introducing a protein sample into the mass spectrometer. Also disclosed herein are new instrumental developments for enhancing the signal from the desired modified proteins, and methods for producing controlled protein fragments in the mass spectrometer eliminating complex microseparations, and protein preparatory chemical steps necessary for cross-linking based protein structure determination using previously available methods.

The preferred method of the present invention involves the determination of the structures of proteins using a top-down analysis of the cross-linked protein to search for covalent modifications wherein intact proteins are ionized and fragmented within the mass spectrometer.

The steps of the preferred method are summarized as follows: exposing a protein to a chemical cross-linker initiating a chemical reaction; terminating the chemical reaction between the protein and the chemical cross-linker; optionally performing buffer exchange to prepare the reaction buffer for electrospray ionization (ESI); introducing the modified protein into an ESI mass spectrometer, or variation thereof; obtaining mass spectral data from the mass spectrometer; analyzing the mass spectrum to identify groups of peaks, based on the mass to charge (m/z) ratios corresponding to unmodified protein, protein monomer with single-ended cross-linker, and protein monomer with a single intramolecular cross-link; isolating one or more charge states of the desired product in the ion trap; fragmenting the species; and patterns of fragments unique to the monomer plus internal cross-links are compared to libraries of possible fragmentation products derived from different possible internal cross-links. Thus, the actual cross-links are determined. The fragmentation and analysis steps may be performed using automated software.

In the preferred method, the modified protein is fragmented and analyzed in a mass spectrometer via at least one of the following methods: infrared multiphoton dissociation (IRMPD), electron capture dissociation (ECD), blackbody infrared radiative dissociation (BIRD), and collision-induced dissociation (CID).

Thus, it is an object of the present invention to provide an improved method of obtaining distance constraints from chemical cross-linking to obtain information about the structure of an intact protein.

Additionally, it is an object of the present invention to analyze protein complexes using fragmentation in a mass spectrometer.

Furthermore, it is an object of the present invention to analyze the structure of protein complexes via electrospray ionization within a mass spectrometer.

Moreover, it is an object of the present invention to analyze the structure of protein complexes by reacting the protein complex with a cross-linker prior to injection in a mass spectrometer.

An additional object of the present invention is to provide a means for the study of the structure/function relationship between proteins, as well as structural changes that occur within proteins upon ligand binding, pH changes, metal ion binding, folding and unfolding, and protein-protein binding.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE FIGURES

For a more complete understanding of the present invention, reference is now made to the following drawings in which:

FIGS. 3A-C show mass spectra of the results of a cross-linking reaction between DSS and carbonic anhydrase with a one-fold molar ratio of DSS to carbonic anyhdrase (FIG. 3A), a two-fold molar ratio of DSS to carbonic anhydrase (FIG. 3B), and a four-fold molar ratio of DSS to carbonic anhydrase (FIG. 3C).

FIGS. 4A-C are expanded views of the m/z 1046 region of FIGS. 3A-C which show that the two-fold molar ratio of cross-linking reagent to protein gives the highest relative concentration of the desired singly internally cross-linked species.

FIGS. 5A-B depict mass spectra of ubiquitin in the absence of a chemical cross-linker (FIG. 5A) and ubiquitin cross-linked with DSS using a two-fold molar excess of DSS to ubiquitin (FIG. 5B).

FIGS. 6A-B are expanded views of FIGS. 5A-B, illustrating the spectral peaks of the internal cross-link and "hanging" cross-linker on ubiquitin (FIG. 6B), along with their respective mass differences to ubiquitin without a cross-link, (FIG. 6A).

FIGS. 7A-D show a comparison of ubiquitin without a cross-linker (FIG. 7A), ubiquitin treated with a two-fold molar excess of DSS (FIG. 7B), an RF isolation sweep (FIG. 7C), and a "gas-phase purified" singly internally cross-linked ubiquitin which has been isolated in the ion trap using the RF isolation sweep in 7C (FIG. 7D).

FIGS. 8A-B show mass spectra of the fragments of ubiquitin produced by infrared multiphoton dissociation (IRMPD) (FIG. 8A) and the fragments of cross-linked ubiquitin produced by IRMPD (FIG. 8B).

FIGS. 9A-F show detailed regions of tandem mass spectrometry (MS/MS) spectra of cross-linked ubiquitin. Shown in FIGS. 9A and 9D are the MS/MS spectra of the cross-linked ubiquitin expanded around the y37 and b52 sequence ions, respectively. Shown in FIGS. 9B and 9E are the MS/MS spectra of ubiquitin taken under the same conditions. The underlined sequences of ubiquitin in FIGS. 9C and 9F correspond to the y37 and b52 ions, respectively. The arrows indicate the lysine residues that are cross-linked.

DETAILED DESCRIPTION OF THE INVENTION

Figure 1C:
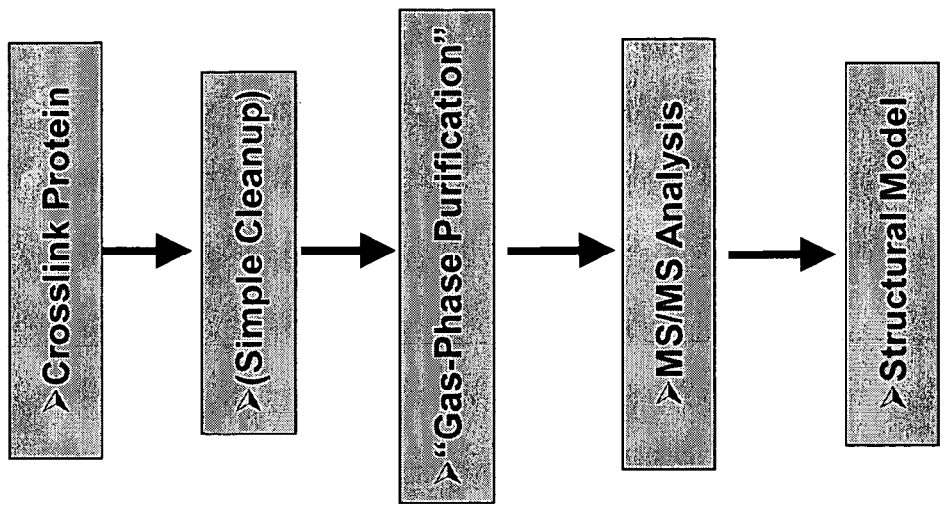
FIGS. 1A-C illustrate the steps in the two approaches to protein cross-linking studies: the "bottom-up" method previously disclosed in the art (FIG. 1A) and the "top-down" method utilized by the present invention (FIGS. 1B-C), where the "top down" method is shown in both pictoral and block diagram form.

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention. The following presents a detailed description of a preferred embodiment (as well as some alternative embodiments) of the present invention.

As used herein, the word "cross-linker" will be defined as follows: any species comprising two reactive groups joined by a linker arm. The length of the linker arm will vary with each cross-linker depending on the number of bonds contained therein. Each of the reactive groups may be designed to react with a particular species within a protein. For example, a reactive group of a cross-linker may be designed to react with a specific amino acid side-chain within a protein. Specific reactive groups may be designed to react with amines, such as lysine, sulfhydryl groups, such as cysteine, carboxyl groups, such as glutamic or aspartic acid, and alcohol groups, such as tyrosine. Nonspecific reactive groups may be designed to react with many more locations within a protein. For example, nonspecific reactive groups may be designed to be photoactivated such that they form nitrene or carbene radicals that insert into adjacent structures. Because cross-linkers generally have two end-groups, they can be classified as specific-specific, specific-nonspecific, or nonspecific-nonspecific, wherein each word of the classification represents the type of end-groups present in the cross-linker.

Moreover, a specific-specific cross-linker may be homo-bifunctional or heterobifunctional. That is, the cross-linker may have identical reactive groups or different reactive groups on each end, respectively. Nonspecific-nonspecific cross-linkers are not often used for the methods of the present invention because of difficulties of obtaining analytical information, i.e., the behavior of the reactive groups may be too nonspecific to yield useful mass spectral data. Nevertheless, some types of nonspecific-nonspecific cross-linkers may prove useful and are consequently within the scope of the present invention.

Numerous mass analyzing systems may be used with the present invention. Such systems include, but are not limited to, Fourier-Transform Ion Cyclotron Resonance (FT-ICR), Quadrupole-Time-of-Flight (Q-TOF), quadrupole trap systems, ion trap, etc. Furthermore, mass selective ion accumulation techniques may be used to enhance the signal from the desired modified proteins while discriminating against ions from low molecular weight species, dimers, impurities, etc.

In particular, the preferred method of the present invention employs a top-down analysis of protein mass spectra to search for covalent modifications. During such analysis intact proteins are ionized and fragmented within the mass spectrometer, or in situ fragmented. The prior art does not disclose in situ fragmentation of cross-linked proteins as a method capable of localizing cross-linked residues in a protein structure for the purpose of obtaining distance constraints to be used in 3-dimensional structure determination.

Instead, prior methods primarily utilize what can be best described as a "bottom-up" approach. As outlined in FIG. 1A, this approach begins with chemical cross-linking, followed by purification, usually by some method of size fractionation, i.e. electrophoresis. Monomers of the desired approximate size are then digested and purified via high-performance liquid chromatography (HPLC), and then measured according to known techniques. The chemical cross-linking reaction may react from thirty minutes to overnight, the purification step may take up to eight hours, protein digestion requires at least thirty minutes, and purification another thirty minutes. The resulting data is analyzed to identify cross-linked fragments, which are then pieced back together similarly to a jigsaw puzzle.

In contrast, the top-down approach to protein cross-linking studies has many potential advantages. Referring to the pictoral and block diagrams of FIGS. 1B and 1C, the monomer separation, proteolytic digestion, and recovery and separation of the proteolytic peptides required by the time-consuming bottom-up approach may all be eliminated in the more efficient top-down approach. Furthermore, the kinetics of the cross-linking reaction may be directly observed in the mass spectra of the whole protein, allowing optimization of the ratio of cross-linking reagent to protein concentration.

Accordingly, the "top-down" method of the present invention will be disclosed in greater detail. It will be appreciated by those of skill in the art that the steps outlined below are exemplary only. Particular steps may be added, modified, or eliminated without departing from the intended scope of the disclosed invention:

The protein 15 to be analyzed is prepared in an active, functional form. Preparation may take place in an aqueous solution, artificial membrane system (such as a liposome or bicelle), or a non-denaturing detergent solution. Preferably, the protein is then exposed to a specific type cross-linker (e.g., specific-specific or specific-nonspecific). Ideally, the stoichiometry between the cross-linker and reactive side groups of the protein, as well as the reaction time, are chosen such that the reaction results in one cross-linker attachment per protein molecule. If the cross-linker can be photoactivated, the reaction mixture is exposed to light at an appropriate intensity and wavelength to render the cross-linker reactive.

The reaction between the cross-linker and the protein is terminated after a suitable time period, which, depending on the specific reaction, may take from thirty minutes to overnight. Various methods of terminating the reaction are possible. For example, an agent can be introduced to the system which binds the cross-linker such that it is unable to further react with the protein. Such an agent may be a solid such that a covalently bound cross-linker and agent complex is formed which can be easily separated out of the system. Furthermore, the agent may bind with free cross-linker, but may also bind with a cross-linker having at least one reactive group which is not attached to a protein. Other methods of the present invention may alter the system conditions such that the reaction no longer proceeds. Such conditions include, but are not limited to, the temperature, pressure, pH, light exposure (i.e., intensity or wavelength of the light the system may be exposed to), etc. Alteration of one or more of these conditions can induce large changes on the reaction rate, and therefore, may be used not only to stop, but also to generally control the reaction between the cross-linker and protein. In some cases, the reaction may be terminated by simply proceeding to the next step.

If the reaction buffer is not already suitable for electrospray ionization (ESI), i.e. the reaction buffer is not sufficiently pure, buffer exchange can be performed to remove non-volatile, basic species, or unreacted cross-linker, a process that may take approximately one minute. A variety of other separation methods may be used to ensure the purity of the sample including, but not limited to, distillation, liquid-liquid extraction, decantation, ion exchange, membrane separation processes, adsorption, etc.

The modified protein is introduced into a mass spectrometer using ESI or variations, such as nanospray or microESI. The choice of mass spectrometer preferably allows the ionized proteins to be subjected to subsequent fragmentation such that the mass-to-charge (m/z) ratios of the products can be determined, for example by using tandem mass spectrometry (MS/MS). Appropriate mass spectrometric systems include, but are not limited to, Fourier-Transform Ion Cyclotron Resonance, Quadrupole-Time-of-Flight, quadrupole trap systems, ion trap systems etc. Furthermore, mass selective ion accumulation techniques may be used to enhance the signal from the desired modified proteins while discriminating against ions from low molecular weight species, dimers, etc. The process of data acquisition takes on the order of ten minutes.

Figure 1B:
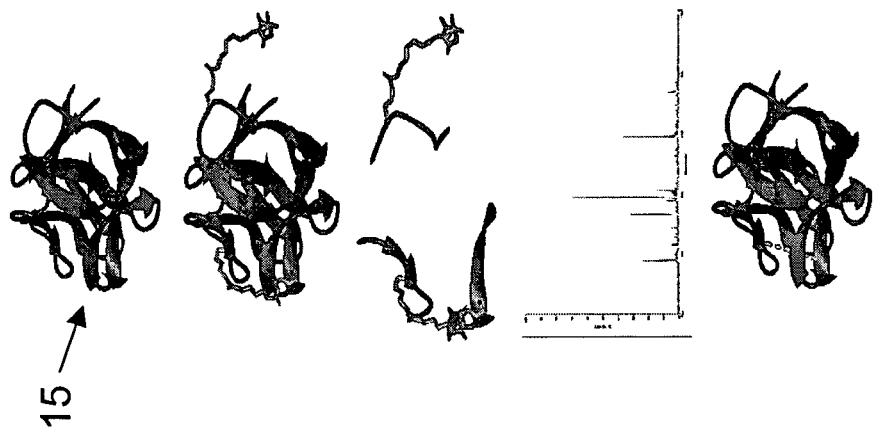
Figure 1A:
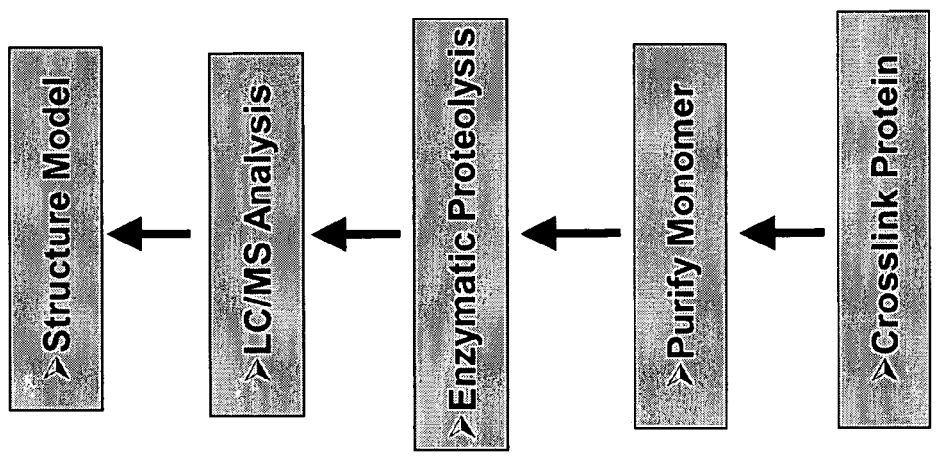

In all, the steps of the present invention, comprising cross-linking and top-down approach, summarily depicted in FIGS. 1B and 1C, may take as little as approximately 45 minutes, whereas a bottom-up approach requires at least several hours. A substantial increase in efficiency is possible with the top-down approach. As important as the increase in efficiency with respect to time, is the reduced number of complex sample handling steps. None of the steps of cross-linking, monomer purification, proteolytic digestion, and HPLC-MS analysis are 100% efficient. Protein will be lost in each step of the bottom-up approach, the reduced number of steps in the top-down approach means that smaller amounts of protein are required for this approach, and it is more amenable to automation.

The mass spectrum of the ionized protein can potentially show peaks at the m/z ratio corresponding to several species: unmodified protein, protein modified with 1, 2, 3, or more cross-linkers, wherein each cross-linker may have reacted with a protein side chain at either one or both ends. Also, any of the modified proteins may have cross-linked to another protein species to form covalent dimers or higher-order multimers.

Groups of peaks corresponding to unmodified protein, protein monomers with single-ended cross-linker, and protein monomer with a single intramolecular cross-link are identified based on their m/z ratios. Note that certain charge states of other monomeric and multimeric mass species may form mass aliases with these species, but only if they have multiple cross-linkers attached. This is shown in the following table:

| Species | Formula | Mass Change Formula | Mass Alias |
|---------|---------|---------------------|------------|
| Unmodified Protein | M+ $(NH_2)_R$ | | |
| Monomer + Single-Ended Crosslink | M+ $(NH_2)_{R-1}$ + NH-CO-L-CO-Q | M+ $(NH_2)_R$ + (CO-L-CO-Q)-H | |
| Monomer + Internal Crosslink | M+ $(NH_2)_{R-2}$ + NH-CO-L-CO-NH | M+ $(NH_2)_R$ + (CO-L-CO)-2H | |
| Dimer + Single-Ended Crosslink | M+ $(NH_2)_{R-1}$ + NH-CO-L-CO-NH+M+ $(NH_2)_{R-1}$ | 2 (M+ $(NH_2)_R$) + (CO-L-CO)-2H | |
| Dimer + Single Crosslink + Open Crosslink | M+ $(NH_2)_{R-1}$ + NH-CO-L-CO-NH+M+ $(NH_2)_{R-2}$ + NH-CO-L-CO-Q | 2 (M+ $(NH_2)_R$) + (CO-L-CO-Q) + (CO-L-CO)-3H | |
| Dimer + Single Crosslink + Internal Crosslink | | 2 (M+ $(NH_2)_R$) + 2 (CO-L-CO)-4H | +2 State Aliases +1 State of Monomer + Internal Crosslink; +4 Aliases +2, etc. | where R is the number of lysine groups, L is the mass of the cross-linker, and Q is the mass of quenching reagent or hydrolysis end product. Note that the only species that has a mass alias for the desirable monomer plus internal crosslink product is the doubly reacted dimer. Under appropriate reaction conditions, the abundance of this dimer species can be made very low, and its relative abundance will be assayable from the half-integral peaks it creates. For higher charge states of monomer, for certain proteins, the dimer will also not be able to take on enough charge, due to proximity effects, to effectively alias the desired monomer properties.

Based on these considerations, one or more charge states of the desired (monomer plus internal crosslink) ion trap. Separation of dimers and higher order species is often not necessary, because the ionization of small amounts of dimer is suppressed in the presence of a large amount of monomer, and experiments have shown that reliable data can be obtained without considering the presence of multimeric protein species.

The selected species is then subjected to fragmentation using a technique such as infrared multiphoton dissociation (IRMPD), electron capture dissociation (ECD), bilinear rotation decoupling (BIRD), or collision-induced dissociation (CID). Typically, control experiments are run with fragmentation of unmodified protein and sometimes monomer with single-ended cross-linker.

Patterns of fragments unique to the monomer plus internal crosslink are compared to libraries of possible fragmentation products derived from different possible internal cross-links. From this, the actually formed cross-links are determined.

All of the fragmentation and analysis described in the previous steps are preferably done by automated software. The automated software also assigns the fragmentation products that are derived from internal cross-links. If the cross-links cannot be uniquely assigned based on the observed fragments, the software may be developed that will automatically cause the fragment of interest to be isolated in the mass spectrometer, unique to ion trapping MS methods such as Fourier Transform Mass Spectrometry (FTMS) to undergo further stages of fragmentation and interpretation to assign the crosslink position.

Numerous variations may be made to each of the steps disclosed above without departing from the scope of the present invention. In terminating the reaction between protein and cross-linker, for example, the unreacted cross-linker may be covalently bonded with a solid to facilitate the cross-linker's removal.

In another alternative method, the modified protein is transferred to a non-denaturing solvent suitable for ESI rather than a denaturing solvent. Also, the use of a water, methanol, and acetic acid mixture for the protein sample may facilitate separation of monomers from dimers and higher-order species, as well as streamline the procedure if the cross-linking reaction is carried out in ESI-compatible buffer.

Moreover, termination and dissolution steps may be combined by injecting the protein sample into a size exclusion chromatography (SEC) column. The column eluate is then analyzed by ESI/MS. This effectively removes free cross-linker and separates monomer and dimer species, thus eliminating the mass aliasing problem. Additionally, electrophoresis may be employed instead of SEC. Also, following the termination and dissolution steps which essentially remove any small molecules, the protein sample may be repeatedly injected into a size exclusion chromatography column.

Appropriately spaced repeated injections are made such that the monomer and dimer peaks do not overlap, allowing improved sensitivity.

Importantly, the present invention is not limited to these variations. Numerous other variations may be made to the steps listed above while remaining within the scope of the present invention as defined by the claims disclosed herein.

Multiple FTMS experiments on proteins have been performed which confirm the methods disclosed herein. Several experiments were performed on carbonic anhydrase and ubiquitin each cross-linked with the amine reactive reagent dissuccinimidyl suberate (DSS). A specific example of an experimental procedure is described below.

A Bruker-Daltonics Apex II FTMS mass spectrometer equipped with a 7.0 Tesla superconducting actively shielded magnet and a Bruker-Daltonics Apollo ESI source were used. The ESI source conditions employed were a drying gas temperature of 100° C. and a nebulizing gas pressure of 60 psi. The source voltages were −4.0 kV on the atmospheric side of the glass capillary and −3.5 kV on the atmospheric chamber end cap shield. The nozzle-skimmer conditions were 100 V (54 V is normal) for the capillary exit voltage and 10 V (approximately 1 V is normal) for the skimmer voltage. The sample concentration was 1-10 micromolar with 6% acetic acid in a 1:1 water/methanol solution.

The sample proteins were cross-linked at a concentration of 1.0 mg/mL in a pH 7.5 trimethyl amine/bicarbonate buffer, where the cross-linking reagent reacts with ammonia and primary amines. The homobifunctional cross-linking reagent dissuccinimidyl suberate (DSS), purchased from Pierce of Rockford, Ill., which reacts with the primary amine on lysine residues, was used at a one-fold, two-fold, and four-fold molar excess to the protein concentration, and the cross-linking reaction was allowed to proceed overnight at room temperature. In order to remove small molecule impurities, the cross-linked samples were subjected to a one-step protein trap cleanup, specifically a Macro Trap purchased from Michrome BioResources of Auburn, Calif. The samples were then diluted to the appropriate concentration for ESI, generally 1-10 micromolar in standard denaturing ESI conditions, 6% acetic acid in a 1:1 water/methanol solution.

The precursor ions were isolated by the multiple Correlated Harmonic Excitation Fields (multi-CHEF) technique. This method serves as a way of isolating ions for dissociation, or a type of gas-phase purification. Multiple charge states can be isolated with the multi-CHEF technique and dissociated with IRMPD. Other methods for isolating ions, such as stored wave-form inverse Fourier transform (SWIFT), could also be used. Both the unmodified protein and the singly cross-linked protein were isolated in separate experiments and fragmented using sustained off-resonance ionization collision induced dissociation (SORI-CID). During SORI-CID, argon gas was pulsed into an analyzer cell to a peak pressure of 1×10-6 mbar, and a 4-8 V p-p RF pulse, with 30-40 dB attenuation, off-resonance from the precursor by 500 Hz, was applied for 250 milliseconds. The attenuation of the SORI-CID RF pulse was adjusted to give nearly complete attenuation of the precursor ion signal. Several seconds were allowed for fragmentation and for pumping away the collision gas so that the fragments could be detected under high-resolution conditions at $1 \times 10^{-9}$ mbar.

Figure 2:
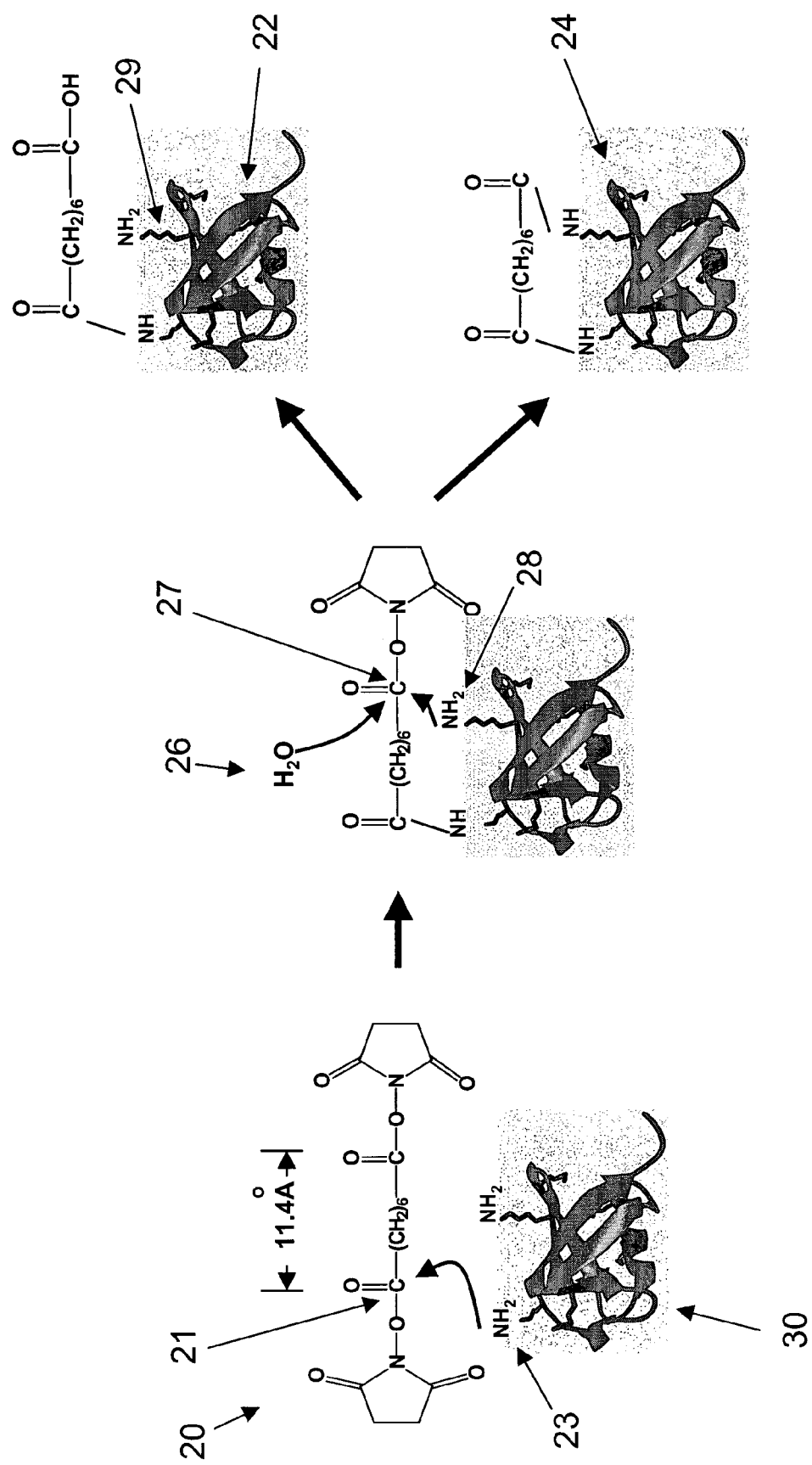
FIG. 2 shows the structures of the disuccinimidyl suberate (DSS) cross-linking reagent and some possible outcomes of the cross-linking reaction.

Referring to FIG. 2, the structure of the DSS cross-linking reagent 20 and the possible outcomes 22 and 24 of the cross-linking reaction are shown. In this case, the nucleophilic nitrogen 23 of the amine group of lysine reacts with the carboxyl carbon 21 of DSS 20. A new bond is formed, thereby linking the cross-linker 20 to the protein 30. From there, a second amine group 28 can react with the other carboxyl carbon 27 of DSS, or a water molecule 26 can react with the second carboxyl carbon 27 of DSS. In the former case, an "internal" cross-link will be formed 24 adding $C_8H_{10}O_2$, and the mass difference to the non-cross-linked protein 30 will be 138.0861 amu. For the latter case, hydrolysis results in a "hanging" cross-link 29 where $C_8H_{12}O_3$ is added to the protein 22, making the mass difference 156.0786 amu. One possible outcome, the hydrolysis of both ends of the cross-linking reagent ultimately consumes any excess cross-linking reagent that does not react with the protein, and is not shown in FIG. 2.

FIGS. 3 and 4 show the results of a cross-linking reaction on carbonic anyhdrase that clearly shows the two-fold molar ratio of cross-linking reagent to protein gives the highest relative concentration of the desired singly internally cross-linked species. With respect to FIG. 3 A-C, graphs of the mass spectrum of the results of a cross-linking reaction on carbonic anhydrase with a one-fold molar ratio of DSS to carbonic anhydrase (FIG. 3A), a two-fold molar ratio of DSS to carbonic anhydrase (FIG. 3B), and a four-fold molar ratio of DSS to carbonic anhydrase (FIG. 3C) are shown with m/z ratios ranging from 700 to 2800. That the use of a two-fold molar ratio is optimum is highlighted in FIGS. 4A-C, which are expanded views of the m/z 1046 region of FIGS. 3A-C. Peak 1 corresponds to one internal cross-link in carbonic anhydrase, and peak 2 corresponds to one "hanging" cross-link. Peaks 3, 4, and 5 are two internal cross-links, one internal and one "hanging" cross-link, and two "hanging" cross-links, respectively. The two-fold molar ratio was also found to be optimum for the proteins myoglobin and ubiquitin.

In the top-down approach, mass spectrometric gas-phase purification, or isolation, and fragmentation of the singly internally cross-linked species replaces many time- and sample-consuming chemical purification steps. FIGS. 5-8 illustrate the top-down procedure for ubiquitin cross-linked with DSS. The fragmentation of both the unmodified and cross-linked ubiquitin was assigned by MS2PRO, a software package developed at Sandia National Laboratories that assigns all possible fragments from a protein, including all internal fragments. MS2PRO also predicts all possible cross-linked species.

With respect to FIGS. 5A-B, graphs of the mass spectra of ubiquitin without a cross-linker (FIG. 5A) and ubiquitin treated with a two-fold molar excess of DSS (FIG. 5B) are shown.

With respect to FIGS. 6 A-B, expanded views of the mass spectra of FIGS. 5 A-B are shown. The peaks 40 with an m/z of 857 correspond to the non-cross-linked ubiquitin, while the peaks 42 with an approximate m/z of 870 correspond to an internal cross-link, and the peaks 44 with an approximate m/z of 873 correspond to a "hanging" cross-link.

With respect to FIGS. 7A-D, four graphs demonstrating the utility of the SWIFT technique in isolating the singly internally cross-linked ubiquitin are shown. FIG. 7A shows a mass spectrum of ubiquitin without a cross-linker, while FIG. 7B shows the mass spectrum of ubiquitin with a two-fold molar excess of the crosslinker DSS. An RF isolation sweep (FIG. 7C) isolates the peaks 46 unique to the singly internally cross-linked ubiquitin. The mass spectrum of this "purified" singly internally cross-linked ubiquitin is shown in FIG. 7D.

Infrared multiphoton dissocation (IRMPD) was used to generate tandem spectra (MS/MS), and the results are depicted in FIGS. 8A-B. The fragments of ubiquitin produced by IRMPD are shown in FIG. 8B, and the fragments of cross-linked ubiquitin produced by IRMPD are shown in FIG. 8A.

FIGS. 9A-F show a detailed region of MS/MS spectra of ubiquitin and cross-linked ubiquitin, with a cross-linked fragment identified, where the fragmentation was performed by SORI-CID. FIG. 9A shows the fragmented singly internally cross-linked ubiquitin expanded around the y37 sequence ion. The isolation of the cross-linked fragment is obvious when compared with FIG. 9B, which shows a spectrum of unmodified ubiquitin fragment taken under the same conditions. The peaks 50 corresponding to the y37 fragment ion of the unmodified ubiguitin appear in both spectra. There are clearly peaks 32 and 34 present at the m/z ratio that corresponds to the y37 ion with a cross-link, that are absent in the MS/MS spectrum of ubiquitin taken under the same conditions. There are only two lysines present in this fragment and since the DSS reagent used for the cross-linking reaction in these experiments only reacts with lysines, these spectra (FIGS. 9A-B) are unequivocal evidence for the formation of a cross-link. The underlined sequence of ubiquitin shown in FIG. 9C corresponds to the y37 ion. The double-headed arrow 48 indicates the lysine residues that are cross-linked. Shown in FIG. 9D is the MS/MS spectra of the cross-linked ubiquitin expanded around the b52 sequence ion. The isolation of the cross-linked fragment is obvious when compared with FIG. 9E, which shows a spectrum of unmodified ubiquitin fragment taken under the same conditions. There are clearly peaks 36 present at the m/z ratio that corresponds to the b52 fragment ion with a cross-link, that are absent in the MS/MS spectrum of ubiquitin taken under the same conditions. There are only two lysines present in this fragment and since the DSS reagent used for the cross-linking reaction in these experiments only reacts with lysines, these spectra (FIGS. 9D-E) are unequivocal evidence for the formation of a cross-link. The underlined sequences of ubiquitin in FIG. 9F corresponds to the b52 ion. The double-headed arrow 54 indicates the lysine residues that are cross-linked.

Figure 10:
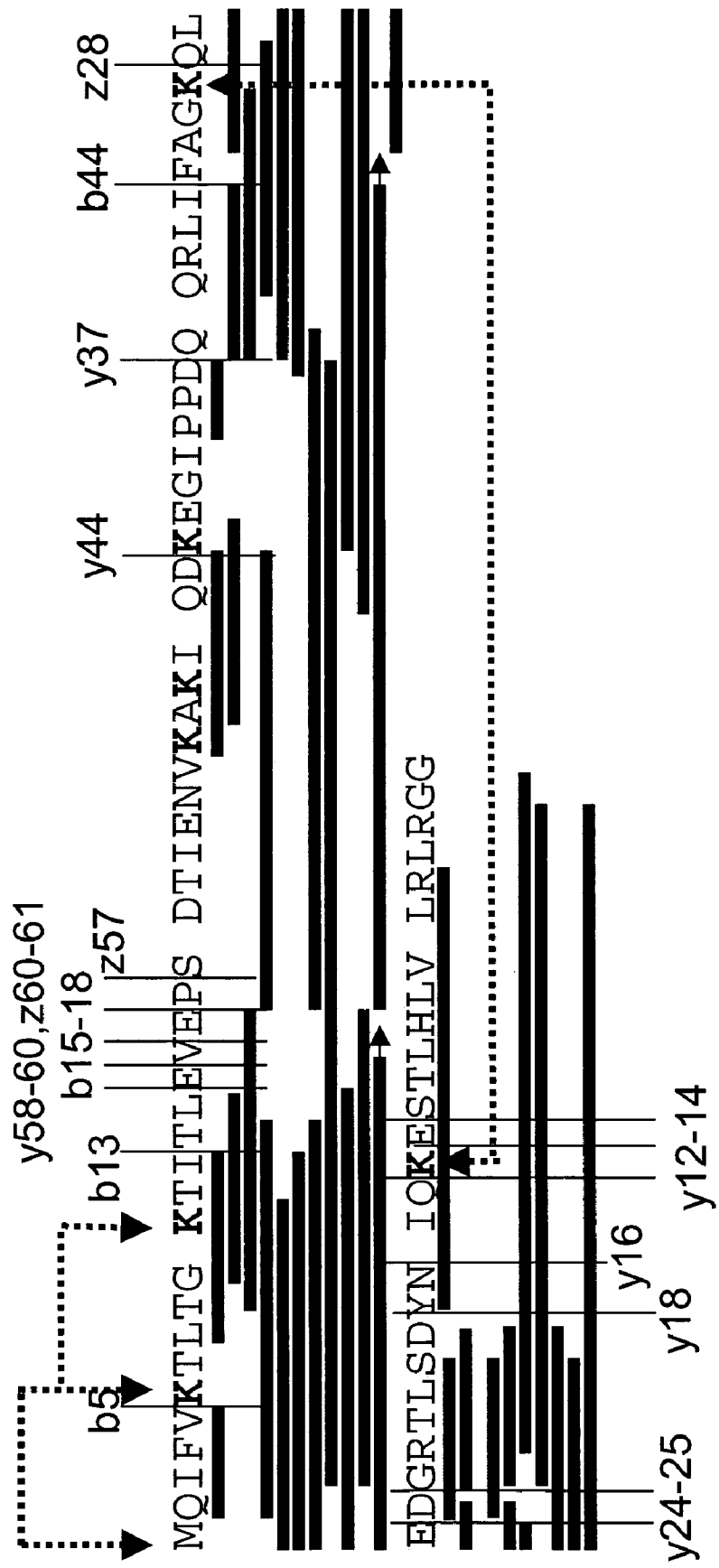
FIG. 10 shows the sequence of ubiquitin, and the sequence coverage achieved by the sustained off-resonance ionization collision induced dissociation (SORI-CID) of the unmodified ubiquitin, where all fragments were assigned by MS2PRO, a software package.

FIG. 10 shows the sequence of ubiquitin, and the sequence coverage achieved by the SORI-CID of the unmodified ubiquitin, where all fragments were assigned by MS2PRO. The cross-linked fragments determined by MS2PRO are summarized in the following table.

| Fragment | [M + H]$^+$ (experimental) | Error (ppm) |
| --- | --- | --- |
| b13 | 1599.1307 | 2.21 |
| y37 | 4391.3838 | 6.12 |
| y58 | 6666.5280 | 0.22 |

Figure 11:
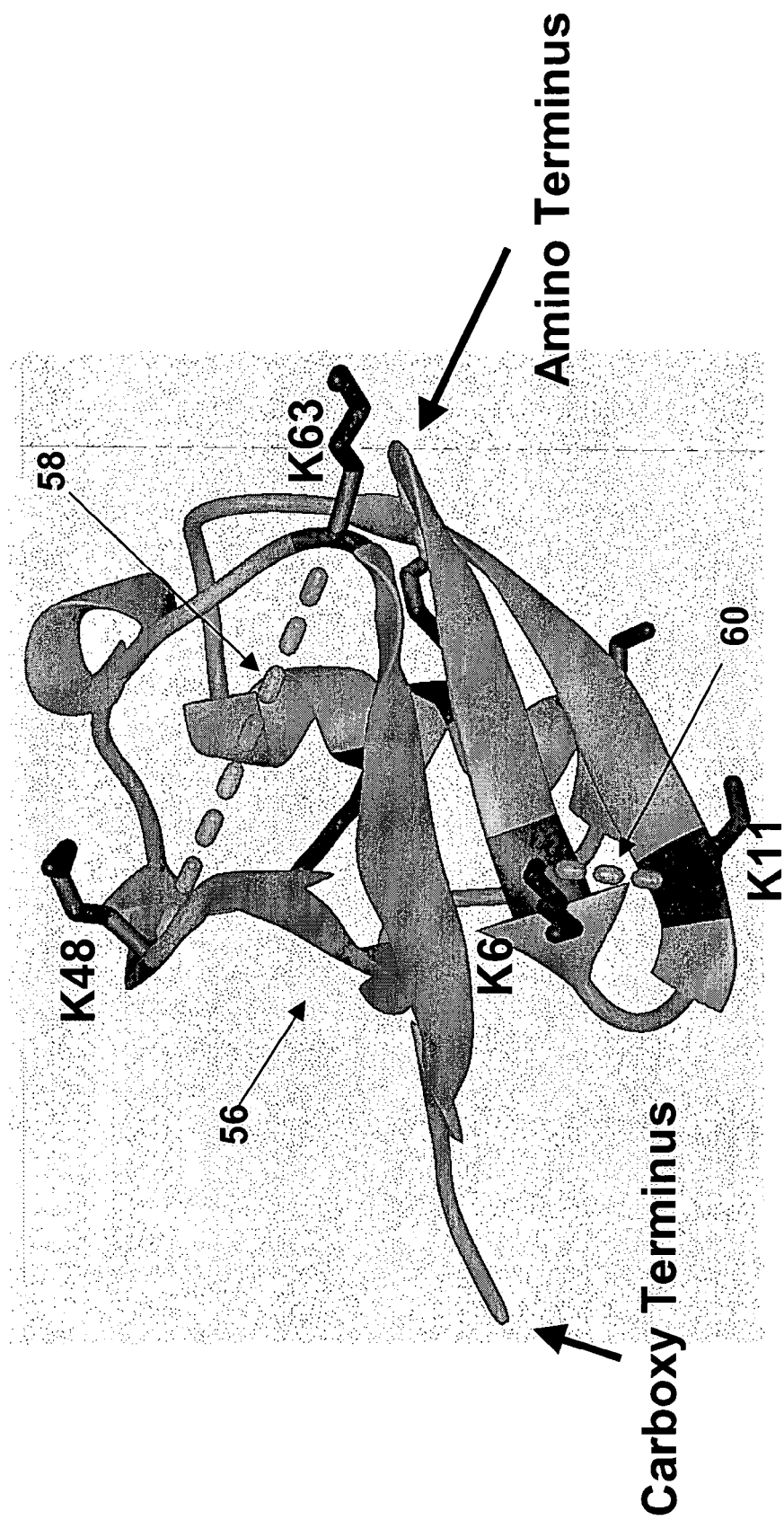
FIG. 11 illustrates the structure of ubiquitin, with cross-links between K6-K11 and K48-K63 illustrated.

FIG. 11 shows the structure of ubiquitin 56 with cross-links 58 and 60 between specific lysine residues as illustrated. Observation of a y37 sequence ion with one cross-link is unambiguous evidence for a K48-K63 cross-link 58. DSS can cross-link lysines up to 24 Å apart and the K48-K63 distance is 17.9 Å in ubiquitin, so the experimental data are consistent with the known protein structure, and also consistent with the intense y58 ion with one internal cross link.

Figure 12:
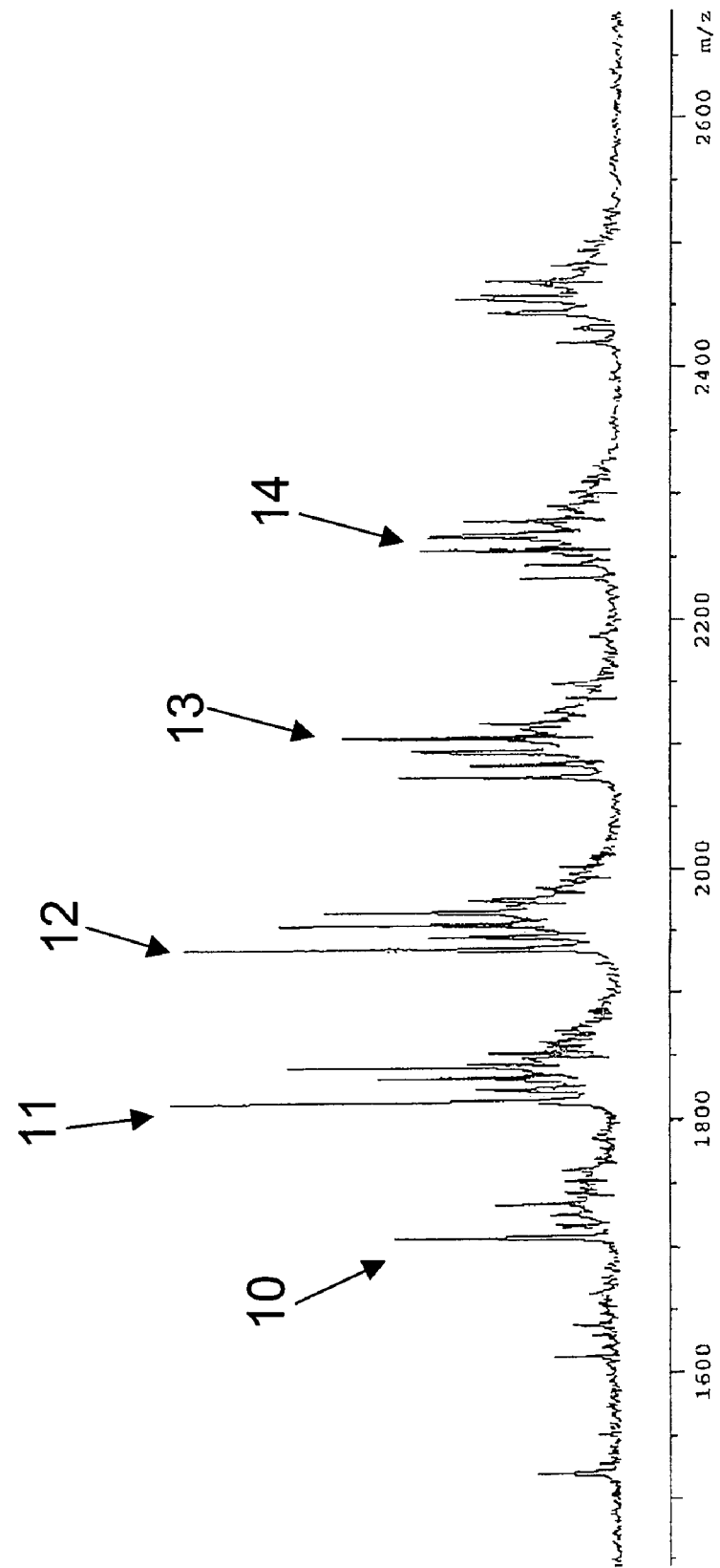
FIG. 12 depicts a mass spectrum recorded without the gas-phase purification of the cross-linked carbonic anhydrase, and the m/z ratio ranging from approximately 1450 to 2700. The carbonic anhydrase sample (1 mg/mL) was prepared in 50 mM of tma/acetate at pH of 5 (buffered to a pH of 8 with TEA), which is reacted with 0.1 M DSS overnight, diluted to 4 times (by volume) into a 1:1 water/methanol 2% acetic acid (400 µL) solution and 20 µL acetic acid added.

Turning last to FIG. 12, shown is a graph of the mass spectrum of the cross-linked carbonic anhydrase, with the m/z scale ranging from about 1450 to 2700. The sample of carbonic anhydrase (1 mg/mL) was prepared from 50 mM of tmalacetate at pH of 5 (buffered to a pH of 8 with TEA), which is reacted with 0.1 M DSS overnight, diluted to 4 times (by volume) into a 1:1 water:methanol 2% acetic acid(400 µL) solution and 20 µL acetic acid. The parent peaks highlighted appear at 1708.6176, with a charge of 17 (10), 1814.8297 with a charge of 16 (11), 1935.7805, with a charge of 15 (12), 2073.9733, with a charge of 14 (13), and 2233.4462, with a charge of 13 (14). A summary of the experimental peaks and calculated molecular weights are shown in the table below.

| Peak 1 | Peak 2 | Charge | Charge | Calc'd MW |
|--------|--------|--------|--------|-----------|
| 1708.6176 | 1814.8297 | 16.9973 | 17 | 29020.87536 |
| 1814.8297 | 1935.7805 | 15.9983 | 16 | 29021.15866 |
| 1935.7805 | 2023.9733 | 15.005  | 15 | 29021.59823 |
| 2023.9733 | 2233.4462 | 13.9989 | 14 | 29021.52421 |
| 2233.4462 | 2419.4831 | 13      | 13 | 29021.70589 |

Based on these values, the average molecular weight of the sample was determined to be 29021.37247. This molecular weight corresponds to the weight of the entire protein and illustrates the use of mass spectrometry on intact proteins.

The carbonic anhydrase sample of FIG. 12 was prepared using the steps previously outlined, but the macro-trap purification, step was omitted. The results shown confirm that the purification procedure is not necessary to obtain good mass spectra to study the cross-linked monomer proteins, if the cross-linking buffers and reagents used are of sufficient purity and compatible with subsequent mass spectrometric analysis. The dimer species created in the cross-linking reactions do not ionize well in the mass spectrometer. If one wished to study the dimers created via cross-linking reactions, the gas phase purification step would be necessary in order to isolate the dimeric species from the other products of the reaction.

While the method and apparatus of the present invention allows for determination of protein structure, the distances between residues of a protein may also be used in different settings. The technique may be useful in structural genomics as a preliminary test to determine the fold-class of a protein. In addition, the present invention serves to enhance the study of protein structural changes, or rearrangements of proteins, the structure-function relationships between proteins, and protein-protein binding.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

What is claimed is:

1. A method for determining protein structure by obtaining the distance between atoms or amino acid residues in a protein, said method comprising the steps of:
   exposing a protein sample to a chemical cross-linker;
   purifying said cross-linked sample;
   introducing said cross-linked sample into a mass spectrometer;
   separating said cross-linked sample into a plurality of cross linked species in the gas phase of said mass spectrometer;
   fragmenting said cross-linked species; and identifying said cross-linked fragments to determine distances between atoms of said protein.

2. A method for determining protein structure by determining the distance between atoms or amino acid residues in a protein, said method comprising the steps of:
   preparing a sample containing a protein in an active, functional form; exposing said sample to a cross-linker such that internal cross-linking of the protein occurs;
   terminating the cross-linking reaction;
   removing unreacted cross-linker;
   dissolving said cross-linked sample in a solvent;
   introducing said cross-linked sample into a mass spectrometer via an ionization technique;
   separating said cross-linked sample into specific cross-linked protein species within said mass spectrometer;
   fragmenting said cross-linked species;
   determining the mass-to-charge ratios of said cross-linked fragments; and
   identifying said cross-linked fragments by comparing the mass-to-charge ratios of said cross-linked fragments to a database of mass-to-charge ratios for known protein fragments.

3. A method according to claim 1, wherein said chemical cross-linker is at least one selected from the group consisting of specific-specific cross-linkers, specific-nonspecific chemical cross-linkers, and nonspecific-nonspecific chemical cross-linkers.

4. A method according to claim 1, wherein said mass spectrometer is at least one selected from the group consisting of a fourier-transform ion cyclotron resonance mass spectrometer, a quadrupole time of flight mass spectrometer, a quadrupole trap mass spectrometer, and an ion trap mass spectrometer.

5. A method according to claim 1, wherein said step of purifying said cross-linked sample comprises a buffer exchange.

6. A method according to claim 1, wherein said step of purifying said cross-linked sample is at least one selected from the group consisting of distillation, liquid-liquid extraction, decantation, ion exchange, membrane separation, and adsorption.

7. A method according to claim 1, wherein said step of introducing said cross-linked sample into a mass spectrometer comprises electrospray ionization.

8. A method according to claim 1, wherein said step of fragmenting said cross-linked species is at least one selected from the group consisting of infrared multiphoton dissociation, electron capture dissociation, bilinear rotation decoupling, and collision-induced dissociation.

9. A method according to claim 1, wherein said step of identifying said cross-linked fragments comprises automated software, wherein said software analyzes a mass spectrum, prepares a list of mass spectrum peaks, reduces the list of mass spectrum peaks to a set of unique masses, compares the set of unique masses to a library of possible fragmentation products derived from possible internal cross-linking possibilities and assigns the set of unique masses to species associated with the fragmentation products found in the library.

10. A method according to claim 1, wherein said step of separating said cross-linked sample into specific cross-linked species comprises the multiple correlated harmonic excitation fields technique.

11. A method according to claim 1, wherein said step of separating said cross-linked sample into specific cross-linked species comprises stored wave-form inverse fourier transform.

12. A method according to claim 2, wherein said chemical cross-linker is at least one selected from the group consisting of specific-specific cross-linkers, specific-nonspecific chemical cross-linkers, and nonspecific-nonspecific chemical cross-linkers.

13. A method according to claim 2, wherein said mass spectrometer is at least one selected from the group consisting of a fourier-transform ion cyclotron resonance mass spectrometer, a quadrupole time of flight mass spectrometer, a quadrupole trap mass spectrometer, and an ion trap mass spectrometer.

14. A method according to claim 2, wherein said step of removing unreacted cross-linker comprises protein trap cleanup.

15. A method according to claim 2, wherein said step of introducing said cross-linked sample into a mass spectrometer comprises electrospray ionization.

16. A method according to claim 2, wherein said step of fragmenting said cross-linked species is at least one selected from the group consisting of infrared multiphoton dissociation, electron capture dissociation, bilinear rotation decoupling, and collision-induced dissociation.

17. A method according to claim 2, wherein said step of identifying said cross-linked fragments comprises automated software, wherein said software analyzes a mass spectrum, prepares a list of mass spectrum peaks, reduces the list of mass spectrum peaks to a set of unique masses, compares the set of unique masses to a library of possible fragmentation products derived from possible internal cross-linking possibilities and assigns the set of unique masses to species associated with the fragmentation products found in the library.

18. A method according to claim 2, wherein said step of separating said cross-linked sample into specific cross-linked species comprises the multiple correlated harmonic excitation fields technique.

19. A method according to claim 2, wherein said step of separating said cross-linked sample into specific cross-linked species comprises stored wave-form inverse fourier transform.

* * * * *